(12) United States Patent
Rao et al.

(10) Patent No.: US 10,176,407 B1
(45) Date of Patent: Jan. 8, 2019

(54) NONLINEAR SPARSE REPRESENTATION-BASED CLASSIFICATION FOR FOVEATED ANALYSIS OF SPECTRAL DATA WITH DISTORTIONS

(71) Applicant: HRL Laboratories, LLC, Malibu, CA (US)

(72) Inventors: Shankar R. Rao, Agoura Hills, CA (US); Yuri Owechko, Newbury Park, CA (US)

(73) Assignee: HRL Laboratories, LLC, Malibu, CA (US)

( * ) Notice: Subject to any disclaimer, the term of this patent is extended or adjusted under 35 U.S.C. 154(b) by 101 days.

(21) Appl. No.: 15/283,358

(22) Filed: Oct. 1, 2016

Related U.S. Application Data

(60) Provisional application No. 62/236,303, filed on Oct. 2, 2015.

(51) Int. Cl.
  *G01N 21/27* (2006.01)
  *G06K 9/62* (2006.01)
  *G06K 9/00* (2006.01)

(52) U.S. Cl.
  CPC ........... *G06K 9/6287* (2013.01); *G01N 21/27* (2013.01); *G06K 9/6277* (2013.01); *G01N 2201/1293* (2013.01); *G06K 2009/00644* (2013.01)

(58) Field of Classification Search
  CPC ..... G01N 21/27; G06K 9/6277; G06K 9/6287
  See application file for complete search history.

(56) References Cited

U.S. PATENT DOCUMENTS

2011/0158046 A1*  6/2011  Ferber et al.  ............ G01V 1/36
367/38

OTHER PUBLICATIONS

D. Ballabio, V. Consonni, "Classification tools in chemistry, Part 1: linear models, PLS-DA," Analytical Methods, vol. 5, No. 16, pp. 3790-3798, 2013.

J. Bioucas-Dias, A. Plaza, G. Camps-Valls, P. Scheunders, N. Nasrabadi, and J. Chanussot, "Hyperspectral remote sensing data analysis and future challenges," IEEE Geoscience & Remote Sensing Magazine, 2013, pp. 6-36.

A. Bruckstein, D. Dohoho, and M. Elad, "From Sparse Solutions of Systems of Equations to Sparse Modeling of Signals and Images," SIAM Review, vol. 51, No. 1, pp. 34-81, 2009.

(Continued)

*Primary Examiner* — Bryan Bui
(74) *Attorney, Agent, or Firm* — Tope-McKay & Associates

(57) ABSTRACT

Described is a system for library-based spectral demixing. The system simultaneously separates and identifies spectral elements in a set of noisy, cluttered spectral elements using Sparse Representation-based Classification (SRC) by modeling the set of noisy, cluttered spectral elements. The spectral library models each spectral element in the set of noisy, cluttered spectral elements, each spectral element having a corresponding wavenumber measurement. Wavenumber measurements are classified, resulting in salient wavenumber measurements. Target spectral elements representing a target of interest are identified in the set of noisy, cluttered spectral elements using the salient wavenumber measurements.

15 Claims, 10 Drawing Sheets

(56) References Cited

OTHER PUBLICATIONS

N. Dobigeon, J.-Y. Tourneret, C. Richard, J. Bermudez, S. McLaughlin, and A. Hero, "Nonlinear Unmixing of Hyperspectral Images: Models and Algorithms," IEEE Signal Processing Magazine, vol. 31, No. 1, pp. 82-94, 2014.

N. Keshava, "A Survey of Spectral Unmixing Algorithms," MIT Lincoln Laboratory Journal, vol. 14, No. 1, pp. 55-78, 2003.

Y. Monakhova, A. Tsikin, S. Mushtakova, and M. Mecozzi, "Independent component analysis and multivariate curve resolution to improve spectral interpretation of complex spectroscopic data sets: Application to infrared spectra of marine organic matter aggregates," Microchemical Journal, vol. 118, pp. 211-222, 2015.

F. Qi, and A.-X. Zhu, "Knowledge discovery from soil maps using inductive learning," Intl. J. Geographical Information Science, vol. 17, No. 8, pp. 771-795, 2010.

A. Wagner, J. Wright, A. Ganesh, Z. Zhou, H. Mobahi, and Y. Ma, "Towards a Practical Face Recognition System: Robust Alignment and Illumination by Sparse Representation," IEEE Trans. on Pattern Analysis and Machine Intelligence (TPAMI), vol. 34, No. 2, pp. 372-386, 2012.

J. Wright, A. Yang, A. Ganesh, S. Sastry, and Y. Ma, "Robust Face Recognition via Sparse Representation," IEEE Trans. on Pattern Analysis and Machine Intelligence (TPAMI), vol. 31. No. 2, 2009, pp. 210-227.

J. Yang and Y. Zhang, "Alternating direction algorithms for L1-problems in compressive sensing," SIAM Journal on Scientific Computing, vol. 33, No. 1-2, pp. 250-278, 2011.

A. Yang, Z. Zhou, A. Ganesh, S. Sastry, and Y. Ma, "Fast l1-Minimization Algorithms for Robust Face Recognition," IEEE Trans. on Image Processing (TIP), 22(8): pp. 3234-3246, 2013.

URI Explosives Database. http://expdb.ohm.uri.edu/ Site last updated on May 1, 2014.

\* cited by examiner

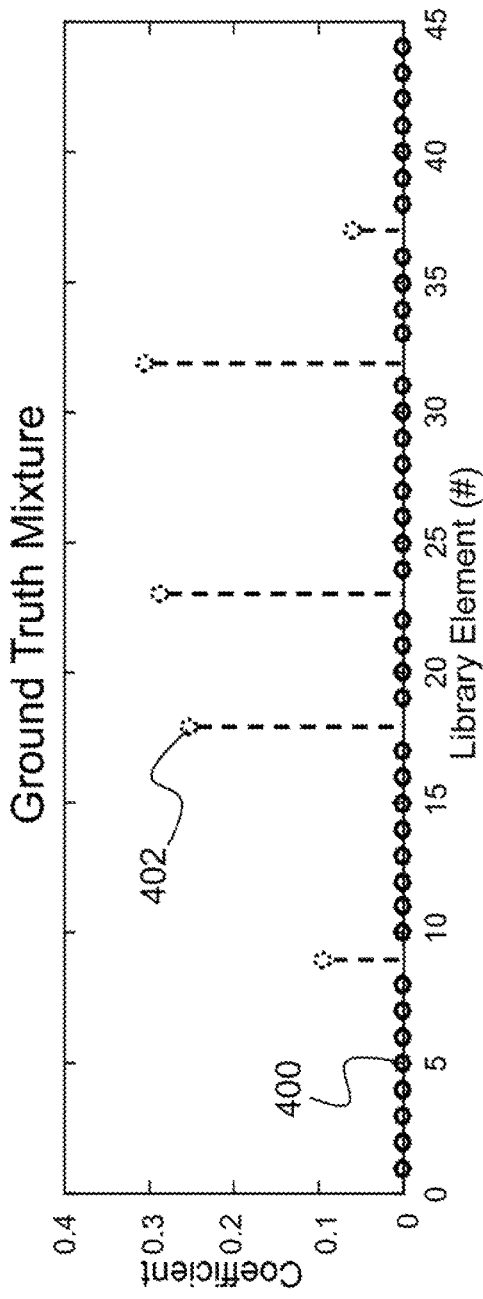
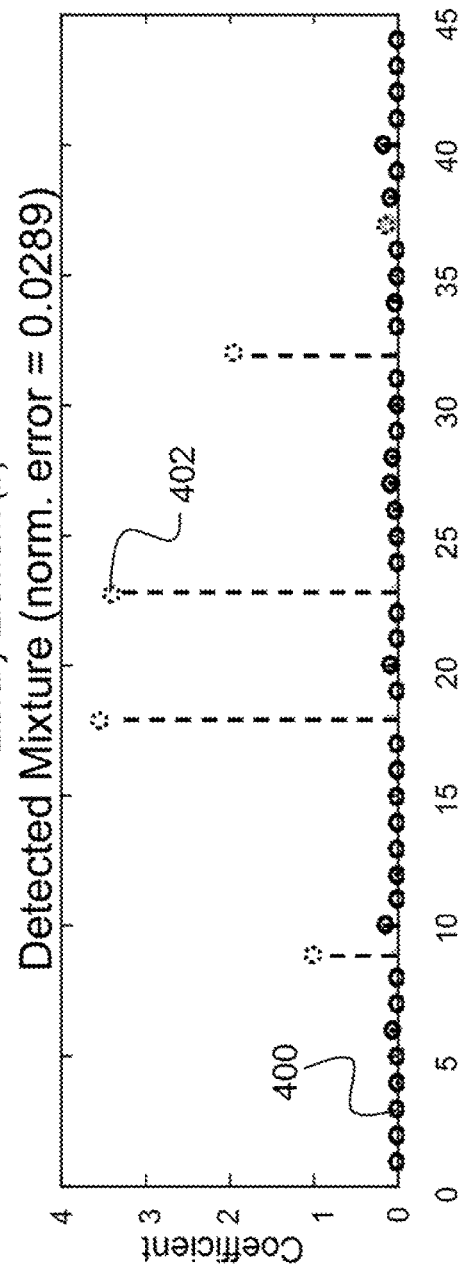
FIG. 4A
FIG. 4B

NONLINEAR SPARSE REPRESENTATION-BASED CLASSIFICATION FOR FOVEATED ANALYSIS OF SPECTRAL DATA WITH DISTORTIONS

CROSS-REFERENCE TO RELATED APPLICATIONS

This is a Non-Provisional application of U.S. Provisional Application No. 62/236,303, filed in the United States on Oct. 2, 2015, entitled, "Nonlinear Sparse Representation-Based Classification for Foveated Analysis of Spectral Data with Distortions," which is incorporated herein by reference in its entirety.

BACKGROUND OF INVENTION

(1) Field of Invention

The present invention relates to a system for library-based spectral demixing and, more particularly, to a system for library-based spectral demixing using a nonlinear extension of Sparse Representation-based Classification (SRC).

(2) Description of Related Art

The detection and analysis of trace chemical residues on surfaces, such as car doors or packages from long stand-off distances (e.g., greater than 1 meter) has not been achievable to date using existing laser-based optical spectroscopy methods due to the high clutter rejection and sensitivity required. Existing algorithmic solutions for stand-off chemical spectrum demixing and identification have utilized methods borrowed from hyperspectral analysis such as vertex component analysis, pixel purity index, and NFINDR (described in Literature Reference No. 2 of the List of Incorporated Literature References), or standard spectrographic methods, such as principal component analysis (PCA) (see Literature Reference No. 1), cross-correlation, partial least squares (PLS), and multivariate curve resolution alternate least squares (MCR-ALS) (see Literature Reference No. 6). These methods involve both a human in the loop and various assumptions, such as the availability of pure material regions to serve as references, which make them inappropriate for automated remote detection of materials and chemical residues.

The spectral demixing problem can be cast as a problem of sparse representation by assuming that the observed spectra can be expressed as a sparse linear combination of a number of pure spectral signatures known in advance (see Literature Reference No. 5). However, the simple linear mixing model is violated for a number of practically occurring phenomena, including variations in illumination angle, humidity, and co-adsorbate interactions. Conventional approaches model the nonlinear interaction of two substrates by augmenting the library of pure spectra with the pairwise products of all library spectra, making the mixing model bilinear (see Literature Reference No. 4). However, such approaches greatly increase the size of the library, and do not scale to interactions of more than two substrates.

Sparse Representation-Based Classification (SRC) was developed by researchers in computer vision for recognizing structured two-dimensional (2D) images, such as faces, in a robust way that can compensate for variabilities due to changes in illumination or pose. A continuing need exists for extending sparse unmixing techniques to include both a parameterized model for nonlinear deformations as well as sparse corruptions for applications in spectral analysis.

SUMMARY OF INVENTION

The present invention relates to a system library-based spectral demixing and, more particularly, to a system for library-based spectral demixing using a nonlinear extension of Sparse Representation-based Classification (SRC). The system comprises one or more processors and a memory having instructions such that when the instructions are executed, the one or more processors perform multiple operations. The system simultaneously separates and identifies spectral elements in a set of noisy, cluttered spectral elements using Sparse Representation-based Classification (SRC) by modeling the set of noisy, cluttered spectral elements using a spectral library. The spectral library models each spectral element in the set of noisy, cluttered spectral elements, each spectral element having a corresponding wavenumber measurement. Wavenumber measurements are classified, resulting in salient wavenumber measurements. Target spectral elements representing a target of interest are identified in the set of noisy, cluttered spectral elements using the salient wavenumber measurements.

In another aspect, given a context for a class of a target of interest, the system discriminates between distinct targets of interest.

In another aspect, given a context for a class of a target of interest, the system discriminates between targets of interest and clutter.

In another aspect, given a context for a class of a target of interest, the system determines which wavenumber measurements are relevant to the target of interest using the context for the class of the target of interest.

In another aspect, foveated nonuniform sampling of salient wavenumber measurements with spectral sensors is used for target of interest identification.

In another aspect, rows of the spectral library that do not correspond to salient wavenumber measurements are pruned.

As can be appreciated by one skilled in the art, in another aspect, the present invention also comprises a method for causing a processor to perform the operations described herein.

Finally, in another aspect, the present invention also comprises a computer program product comprising computer-readable instructions stored on a non-transitory computer-readable medium that are executable by a computer having a processor for causing the processor to perform the operations described herein.

BRIEF DESCRIPTION OF THE DRAWINGS

The objects, features and advantages of the present invention will be apparent from the following detailed descriptions of the various aspects of the invention in conjunction with reference to the following drawings, where:

FIG. 4A illustrates SRC-based demixing and denoising of a mixture of target spectra with ground truth mixture coefficients according to various embodiments of the present disclosure;

FIG. 4B illustrates SRC-based demixing and denoising of a mixture of target spectra with mixing coefficients reconstructed using SRC according to various embodiments of the present disclosure;

DETAILED DESCRIPTION

Figure 1:
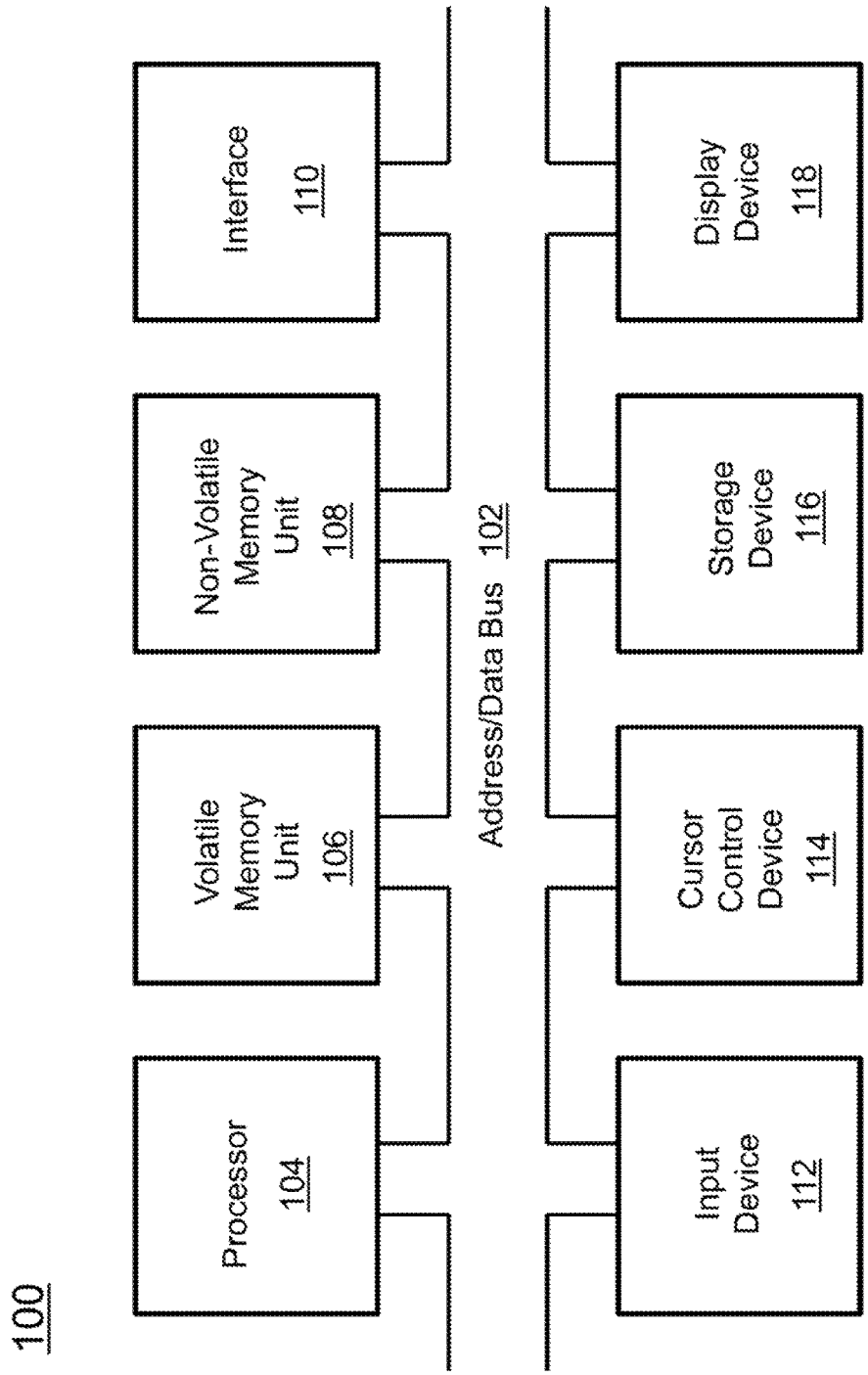
FIG. 1 is a block diagram depicting the components of a system for spectral demixing according to various embodiments of the present disclosure.

The present invention is a system library-based spectral demixing and, more particularly, to a system for library-based spectral demixing using a nonlinear extension of Sparse Representation-based Classification (SRC). The following description is presented to enable one of ordinary skill in the art to make and use the invention and to incorporate it in the context of particular applications. Various modifications, as well as a variety of uses in different applications will be readily apparent to those skilled in the art, and the general principles defined herein may be applied to a wide range of aspects. Thus, the present invention is not intended to be limited to the aspects presented, but is to be accorded the widest scope consistent with the principles and novel features disclosed herein.

In the following detailed description, numerous specific details are set forth in order to provide a more thorough understanding of the present invention. However, it will be apparent to one skilled in the art that the present invention may be practiced without necessarily being limited to these specific details. In other instances, well-known structures and devices are shown in block diagram form, rather than in detail, in order to avoid obscuring the present invention.

The reader's attention is directed to all papers and documents which are filed concurrently with this specification and which are open to public inspection with this specification, and the contents of all such papers and documents are incorporated herein by reference. All the features disclosed in this specification, (including any accompanying claims, abstract, and drawings) may be replaced by alternative features serving the same, equivalent or similar purpose, unless expressly stated otherwise. Thus, unless expressly stated otherwise, each feature disclosed is one example only of a generic series of equivalent or similar features.

Furthermore, any element in a claim that does not explicitly state "means for" performing a specified function, or "step for" performing a specific function, is not to be interpreted as a "means" or "step" clause as specified in 35 U.S.C. Section 112, Paragraph 6. In particular, the use of "step of" or "act of" in the claims herein is not intended to invoke the provisions of 35 U.S.C. 112, Paragraph 6.

Before describing the invention in detail, first a list of cited references is provided. Next, a description of the various principal aspects of the present invention is provided. Finally, specific details of various embodiment of the present invention are provided to give an understanding of the specific aspects.

(1) List of Incorporated Literature References

The following references are cited and incorporated throughout this application. For clarity and convenience, the references are listed herein as a central resource for the reader. The following references are hereby incorporated by reference as though fully set forth herein. The references are cited in the application by referring to the corresponding literature reference number.

1. D. Ballabio, V. Consonni, "Classification tools in chemistry, Part 1: linear models, PLS-DA," Analytical Methods, Vol. 5, No. 16, pp. 3790-3798, 2013.

2. J. Bioucas-Dias, A. Plaza, G. Camps-Valls, P. Scheunders, N. Nasrabadi, and J. Chanussot, "Hyperspectral remote sensing data analysis and future challenges," IEEE Geoscience & Remote Sensing Magazine, 2013.

3. A. Bruckstein, D. Dohoho, and M. Elad, "From Sparse Solutions of Systems of Equations to Sparse Modeling of Signals and Images," SIAM Review, Vol. 51, No. 1,pp. 34-81, 2009.

4. N. Dobigeon, J. Y. Tourneret, C. Richard, J. Bermudez, S, McLaughlin, and A. Hero, "Nonlinear Ummixing of Hyperspectral Images: Models and Algorithms," IEEE Signal Processing Magazine, Vol. 31. No. 1. pp. 82-94, 2014.

5. N. Keshava, "A Survey of Spectral Unmixing Algorithms," MIT Lincoln Laboratory Journal, Vol. 14, No. 1, pp. 55-78, 2003.

6. Y. Monakhova, Tsikin, S. Mushtakova, and M. Mecozzi, "Independent component analysis and multivariate curve resolution to improve spectral interpretation of complex spectroscopic data sets: Application to infrared spectra of marine organic matter aggregates," Microchemical Journal, Vol. 118, pp. 211-222, 2015.

7. F. Qi, and A. X. Zhu, "Knowledge discovery from soil maps using inductive learning," Intl. J. Geographical Information Science, Vol. 17, No. 8, 771-795, 2010.

8. A. Wagner, J. Wright, A. Ganesh, Z. Zhou, H. Mobahi, and Y. Ma, "Towards a Practical Face Recognition System: Robust Alignment and Illumination by Sparse Representation," IEEE Trans. on Pattern Analysis and Machine Intelligence (TPAMI), Vol. 34, No. 2, pp. 372-386, 2012.

9. J. Wright, A. Yang, A. Ganesh, S. Sastry, and Y. Ma, "Robust Face Recognition via Sparse Representation," IEEE Trans. on Pattern Analysis and Machine Intelligence (TPAMI), Vol. 31. No. 2, 2009.

10. J. Yang and Y. Zhang, "Alternating direction algorithms for L1-problems in compressive sensing," SIAM Journal on Scientific Computing, Vol. 33, No. 1-2, pp. 250-278, 2011.

11. A. Yang, Z. Zhou, A. Ganesh, S. Sastry, and Y. Ma, "Fast l1-Minimization Algorithms for Robust Face Recognition," IEEE Trans. on Image Processing (TIP), 22(8): 3234-3246, 2013.

(2) Principal Aspects

Various embodiments of the invention include three "principal" aspects. The first is a system for spectral demixing. The system is typically in the form of a computer system operating software or in the form of a "hard-coded" instruction set. This system may be incorporated into a wide variety of devices that provide different functionalities. The second principal aspect is a method, typically in the form of software, operated using a data processing system (computer). The third principal aspect is a computer program product. The computer program product generally represents computer-readable instructions stored on a non-transitory computer-readable medium such as an optical storage device, e.g., a compact disc (CD) or digital versatile disc (DVD), or a magnetic storage device such as a floppy disk or magnetic tape. Other, non-limiting examples of computer-readable media include hard disks, read-only memory (ROM), and flash-type memories. These aspects will be described in more detail below.

A block diagram depicting an example of a system (i.e., computer system 100) of the present invention is provided in FIG. 1. The computer system 100 is configured to perform calculations, processes, operations, and/or functions associated with a program or algorithm. In one aspect, certain processes and steps discussed herein are realized as a series of instructions (e.g., software program) that reside within computer readable memory units and are executed by one or more processors of the computer system 100. When executed, the instructions cause the computer system 100 to perform specific actions and exhibit specific behavior, such as described herein.

The computer system 100 may include an address/data bus 102 that is configured to communicate information. Additionally, one or more data processing units, such as a processor 104 (or processors), are coupled with the address/data bus 102. The processor 104 is configured to process information and instructions. In an aspect, the processor 104 is a microprocessor. Alternatively, the processor 104 may be a different type of processor such as a parallel processor, application-specific integrated circuit (ASIC), programmable logic array (PLA), complex programmable logic device (CPLD), or a field programmable gate array (FPGA).

The computer system 100 is configured to utilize one or more data storage units. The computer system 100 may include a volatile memory unit 106 (e.g., random access memory ("RAM"), static RAM, dynamic RAM, etc.) coupled with the address/data bus 102, wherein a volatile memory unit 106 is configured to store information and instructions for the processor 104. The computer system 100 further may include a non-volatile memory unit 108 (e.g., read-only memory ("ROM"), programmable ROM ("PROM"), erasable programmable ROM ("EPROM"), electrically erasable programmable ROM "EEPROM"), flash memory, etc.) coupled with the address/data bus 102, wherein the non-volatile memory unit 108 is configured to store static information and instructions for the processor 104. Alternatively, the computer system 100 may execute instructions retrieved from an online data storage unit such as in "Cloud" computing. In an aspect, the computer system 100 also may include one or more interfaces, such as an interface 110, coupled with the address/data bus 102. The one or more interfaces are configured to enable the computer system 100 to interface with other electronic devices and computer systems. The communication interfaces implemented by the one or more interfaces may include wireline (e.g., serial cables, modems, network adaptors, etc.) and/or wireless (e.g., wireless modems, wireless network adaptors, etc.) communication technology.

In one aspect, the computer system 100 may include an input device 112 coupled with the address/data bus 102, wherein the input device 112 is configured to communicate information and command selections to the processor 100. In accordance with one aspect, the input device 112 is an alphanumeric input device, such as a keyboard, that may include alphanumeric and/or function keys. Alternatively, the input device 112 may be an input device other than an alphanumeric input device. In an aspect, the computer system 100 may include a cursor control device 114 coupled with the address/data bus 102, wherein the cursor control device 114 is configured to communicate user input information and/or command selections to the processor 100. In an aspect, the cursor control device 114 is implemented using a device such as a mouse, a track-ball, a track-pad, an optical tracking device, or a touch screen. The foregoing notwithstanding, in an aspect, the cursor control device 114 is directed and/or activated via input from the input device 112, such as in response to the use of special keys and key sequence commands associated with the input device 112. In an alternative aspect, the cursor control device 114 is configured to be directed or guided by voice commands.

In an aspect, the computer system 100 further may include one or more optional computer usable data storage devices, such as a storage device 116, coupled with the address/data bus 102. The storage device 116 is configured to store information and/or computer executable instructions. In one aspect, the storage device 116 is a storage device such as a magnetic or optical disk drive (e.g., hard disk drive ("HDD"), floppy diskette, compact disk read only memory ("CD-ROM"), digital versatile disk ("DVD")). Pursuant to one aspect, a display device 118 is coupled with the address/data bus 102, wherein the display device 118 is configured to display video and/or graphics. In an aspect, the display device 118 may include a cathode ray tube ("CRT"), liquid crystal display ("LCD"), field emission display ("FED"), plasma display, or any other display device suitable for displaying video and/or graphic images and alphanumeric characters recognizable to a user.

The computer system 100 presented herein is an example computing environment in accordance with an aspect. However, the non-limiting example of the computer system 100 is not strictly limited to being a computer system. For example, an aspect provides that the computer system 100 represents a type of data processing analysis that may be used in accordance with various aspects described herein. Moreover, other computing systems may also be implemented. Indeed, the spirit and scope of the present technology is not limited to any single data processing environment, Thus, in an aspect, one or more operations of various aspects of the present technology are controlled or implemented using computer-executable instructions, such as program modules, being executed by a computer. In one implementation, such program modules include routines, programs, objects, components and/or data structures that are configured to perform particular tasks or implement particular abstract data types. In addition, an aspect provides that one or more aspects of the present technology are implemented by utilizing one or more distributed computing environments, such as where tasks are performed by remote processing devices that are linked through a communications network, or such as where various program modules are located in both local and remote computer-storage media including memory-storage devices.

Figure 2:
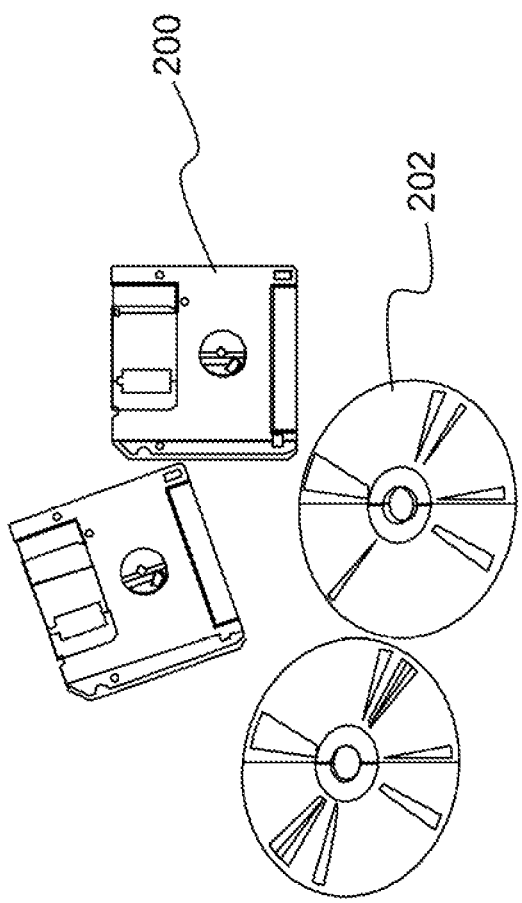
FIG. 2 is an illustration of a computer program product according to various embodiments of the present disclosure.

An illustrative diagram of a computer program product (i.e., storage device) embodying the present invention is depicted in FIG. 2. The computer program product is depicted as floppy disk 200 or an optical disk 202 such as a CD or DVD. However, as mentioned previously, the computer program product generally represents computer-readable instructions stored on any compatible non-transitory computer-readable medium. The term "instructions" as used with, respect to this invention generally indicates a set of operations to be performed on a computer, and may represent pieces of a whole program or individual, separable, software modules. Non-limiting examples of "instruction" include computer program code (source or object code) and "hard-coded" electronics (i.e. computer operations coded into a computer chip). The "instruction" is stored on any non-transitory computer-readable medium, such as in the memory of a computer or on a floppy disk, a CD-ROM, and a flash drive. In either event, the instructions are encoded on a non-transitory computer-readable medium.

(3) Specific Details of Various Embodiments

Described is a system for performing library-based spectral demixing using a unique nonlinear extension of Sparse Representation-based Classification (SRC) originally developed for pose-robust face recognition from digital images. The detection and analysis of trace chemical residues on surfaces from long stand-off distances has not been achievable to date using existing laser-based spectroscopy methods due to the high clutter rejection and sensitivity required. The system according to various embodiments of the present disclosure uses SRC to model a set of noisy spectral measurements as a combination of elements from the spectral library for classification of the mixture components using sparsity-optimizing $L_1$ norm minimization. SRC is adapted to leverage "foveated" non-uniform spectral sampling of the most salient wavenumber measurements for target identification and discrimination from clutter. SRC simultaneously separates and identifies mixture components by modeling the mixture using a spectral library and $L_1$ norm minimization.

SRC is robust to noise and sparse corruptions and can model and correct for certain kinds of nonlinear deformations, such as the effects of different substrates on measured target spectra. This enables SRC to achieve both high probability of detection (Pd) (>95%) and low false alarm rate ($P_{fa}$) (<$10^{-4}$) despite significant measurement noise (peak signal-to-noise ratio (PSNR)>25 decibels (dB)) and clutter (target concentrations <1% of mixture).

Given a vector y containing the measured spectra at d wavelengths (with measurement noise variance $\sigma^2$), demixing of y amounts to finding an optimal set of n linear mixture coefficients contain in a sparse vector x (i.e., most of the coefficients in x are zero) with respect to (potentially very large) spectral library A that can best model each mixed spectral element in the signal. Here, A is an n×d matrix whose columns represent d-dimensional spectra templates each column for n targets.

Though this sparse representation problem is combinatorial in general, under mild assumptions on A, the minimum L1-norm solution x* given by:

$$x^* = \underset{x}{\operatorname{argmin}} \|x\|_1 \text{ subj. to } \|y - Ax\|_2^2 \leq \sigma^2$$

is also the sparsest solution to the system (see Literature Reference No. 3). Here, $\|\cdot\|_1$ is the L1-norm (absolute sum of entries), $\|\cdot\|_2^2$ is the squared Euclidean norm, argmin denotes the argument of the minimum, and subj. denotes "subject". The past decade has seen an explosion in the development of efficient algorithms for solving the above $L_1$-minimization and related objective functions to recover a provably optimal sparse representation as described in Literature Reference Nos. 10 and 11.

More recently, the machine learning community has examined pattern recognition within a sparse representation-based classification (SRC) framework The basic approach, first proposed in Literature Reference No. 9, stipulates that even with an extremely low sampling rate and severe signal corruption, the category of a target of interest y can be recognized by seeking a sparse representation with respect to all the training examples of K categories according to the following:

$$(x^*, e^*) = \underset{x,e}{\operatorname{argmin}} \|x\|_1 + \|e\|_1$$

$$\text{subj. to } \left\| y - \underbrace{[A_1, A_2, \ldots, A_K]}_{A} x - e \right\|_2^2 \leq \sigma^2,$$

where the dominant nonzero coefficients in x* correspond to the category of the query signal y, and e* models the sparse elements in y that cannot be well modeled by the library A. The robust SRC framework is easily extended to demixing by removing the restriction that the coefficient vector x is concentrated in only one of the K categories.

Thus, analogous to the approach for pose-invariant robust object recognition in computer vision described in Literature Reference No. 8, in the system according to embodiments of the present disclosure, the above sparse demixing framework is extended to laser absorption spectroscopy by including nonlinear deformations of the spectrum due to different substrates and probe laser angles of incidence according to the following:

$$(x^*, e^*, \tau^*) = \underset{x,e}{\operatorname{argmin}} \|x\|_1 + \|e\|_1$$

$$\text{subj. to } \|y \circ \tau - Ax - e\|_2^2 \leq \sigma^2.$$

Here, $\tau$ models a class of deformations of the input signal y. Given a smooth parameterized function form for $\tau$, this nonconvex optimization problem can be effectively solved for a large range of initial conditions by solving a sequence of convex optimizations problems that iteratively linearize about the current estimate of $\tau$ according to the following:

$$(x^*, e^*, \Delta\tau^*) = \underset{x,e,\Delta\tau}{\operatorname{argmin}} \|x\|_1 + \|e\|_1$$

$$\text{subj. to } \|y \circ \tau^j + J\Delta\tau - Ax - e\|_2^2 \leq \sigma^2$$

$$\tau^{j+1} = \tau^j + \Delta\tau^*,$$

where $$J = \frac{\partial}{\partial \tau} y \circ \tau$$

is the Jacobian of y°τw.r.t. τ, and Δτ is the step in τ. As supported in Literature Reference No. 8, a large class of smooth deformations can be modeled and corrected using the above approach using 10-15 iterations. The parameterized models used in Literature Reference No. 8 enable SRC-based face recognition to be robust to variations in pose (e.g., rotation, translation, and perspective changes). In the spectral demixing application according to various embodiments of the present disclosure, analogous parameterized models can be used to demix and identify target spectra that have been deformed due to variations in humidity, illuminations, and interactions between coadsorbates (substances absorbed) and substrates.

In accordance with various embodiments of the present disclosure, SRC was further adapted for rapid, real-time spectral target identification with a large spectral library by making use of non-uniformly sampled "foveated" measurements. Provided a context for the class of targets of interest (e.g., foliage, minerals, narcotics, explosives), one can use that contextual prior knowledge to determine which wavelengths are most relevant for discriminating between different targets and between targets and clutter (e.g., selecting wavelengths corresponding to known target peaks or using automated feature selection methods, such as decision trees (see Literature Reference No. 7)). This reduced set of wavelengths can be acquired more rapidly from a spectral sensor, and the sparse optimization used for identification can be sped up by pruning the rows of the spectral library A that do not correspond to wavelengths of interest (see FIG. 7 for results using foveated measurements).

Figure 3:
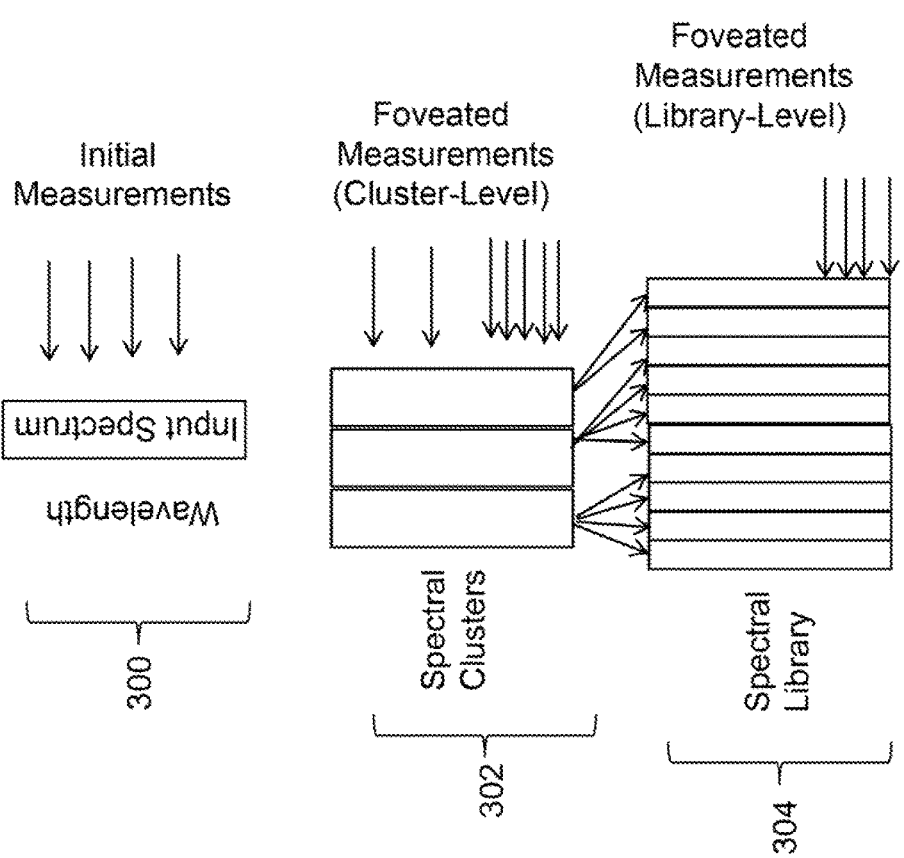
FIG. 3 is an illustration of an example of nonuniform foveated measurements that can be leveraged by Sparse Representation-based Classification (SRC) to rapidly identify targets in a spectral library according to various embodiments of the present disclosure.

SRC can also be applied in an active system without prior contextual knowledge by organizing the library into a tree structure and then traversing the tree structure using adaptive spectral measurements. A notional example of this process is shown in FIG. 3, which depicts nonuniform foveated measurements that can be leveraged by SRC to rapidly identify targets in a large spectral library in an adaptive, hierarchical fashion. Initially, coarse uniform spectral measurements 300 is taken over the entire bandwidth, and SRC is used on these coarse measurements to determine which cluster the input spectra belong to (i.e., spectral clusters 302). Based on the detected cluster, the next set of measurements is adapted to provide maximum discriminate capability within the cluster (i.e., spectral library 304). At each level of the tree, a reduced instance of SRC (by pruning both wavelengths and library elements from A) is solved to determine which node of the tree to traverse, performing final target identification when the leaf nodes of the tree are reached.

In the following simulations, the effectiveness of the SRC representation framework according to various embodiments of the present disclosure is demonstrated for simultaneous spectral denoising, demixing and identification. The library for simulations was constructed using 44 spectral signals obtained from the University of Rhode Island (URI) Explosives Database measured at wavenumbers in the range $v \in \{650, 4000\}$ cm$^{-1}$. In the first experimental study, multi-target detection performance in the presence of varying amounts of measurement noise was examined. Uniformly distributed random mixing weights x were generated with 5 nonzero coefficients (corresponding to the 5 targets in the mixture), where all nonzero coefficients $x_i \geq 0.01$ (i.e, 1% target concentration), and then random Gaussian noise with PSNR ranging from 12 dB to 30 dB was added. The sparse coefficients for each component in the mixture were recovered using the YALL1 algorithm, an efficient solver for the above L1 minimization problem as described in Literature Reference No. 10). For each noise level, each simulation was repeated 500 times.

Figure 4C:
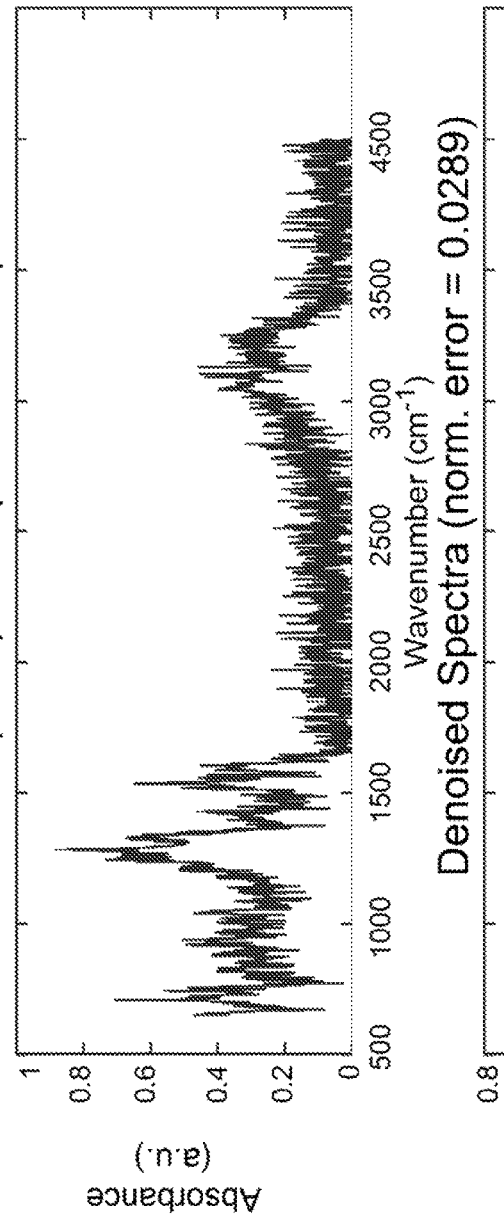
FIG. 4C illustrates noisy input spectra according to various embodiments of the present disclosure.
Figure 4D:
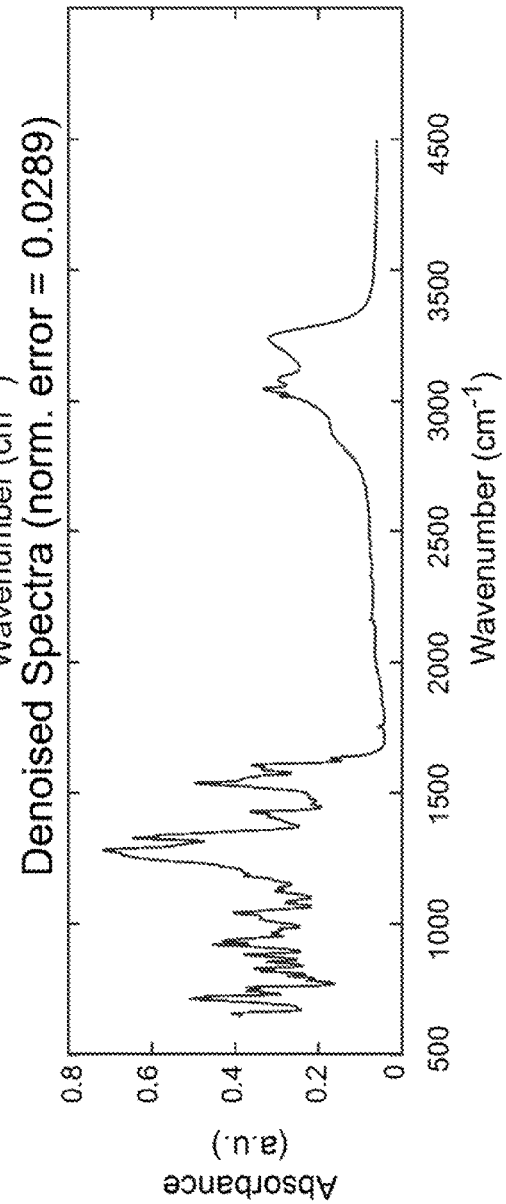
FIG. 4D illustrates spectra denoised by SRC according to various embodiments of the present disclosure.

Examples for demixing and denoising mixtures in noise with PSNR 12 dB are illustrated in FIGS. 4A-4D. FIGS. 4A-4D illustrate SRC-based demixing and denoising of an example mixture of 5 target spectra from a library of 44 explosives and 12 db measurement PSNR. FIG. 4A depicts demixing and denoising of ground truth mixture coefficients, and FIG. 4B depicts demixing and denoising of mixing coefficients reconstructed using SRC, where solid circles 400 represent non-targets and dashed circles 402 represent targets. The normalized reconstruction error ($\|y-\hat{y}\|/\|y\|$) was 0.029. A comparison of the noisy input spectra is shown in FIG. 4C with the spectra denoised by SRC shown in FIG. 4D.

Figure 5:
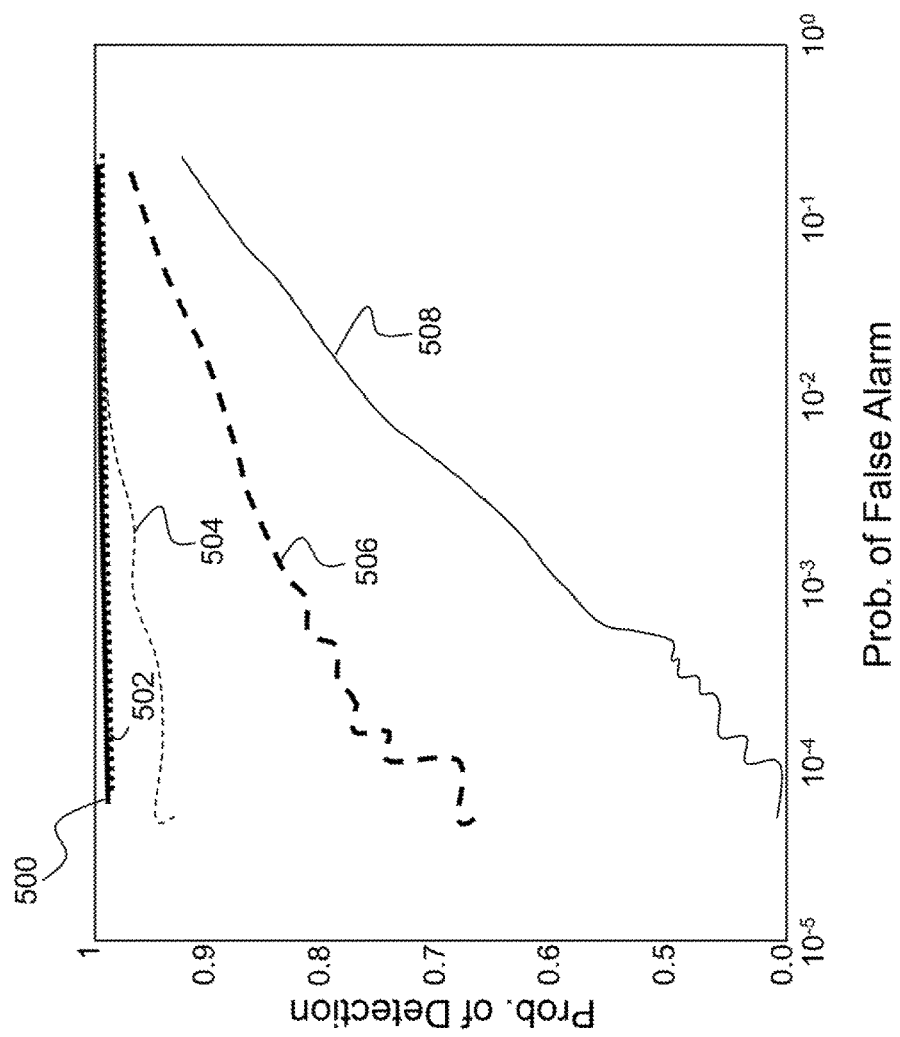
FIG. 5 illustrates a comparison of probability of detection versus probability of false alarms on simulated mixtures of target spectra for varying noise levels according to various embodiments of the present disclosure.

FIG. 5 is a plot depicting a comparison of SRC $P_d$ (probability of detection) versus $P_{fa}$ (probability of false alarm) performance on simulated mixtures of 5 target spectra from a library of 44 explosives for varying noise levels (PSNR=30 dB (represented by curve 500), 25 dB (represented by curve 502), 20 dB (represented by curve 504), 15 dB (represented by curve 506), and 12 dB (represented by curve 508)).

Figure 6:
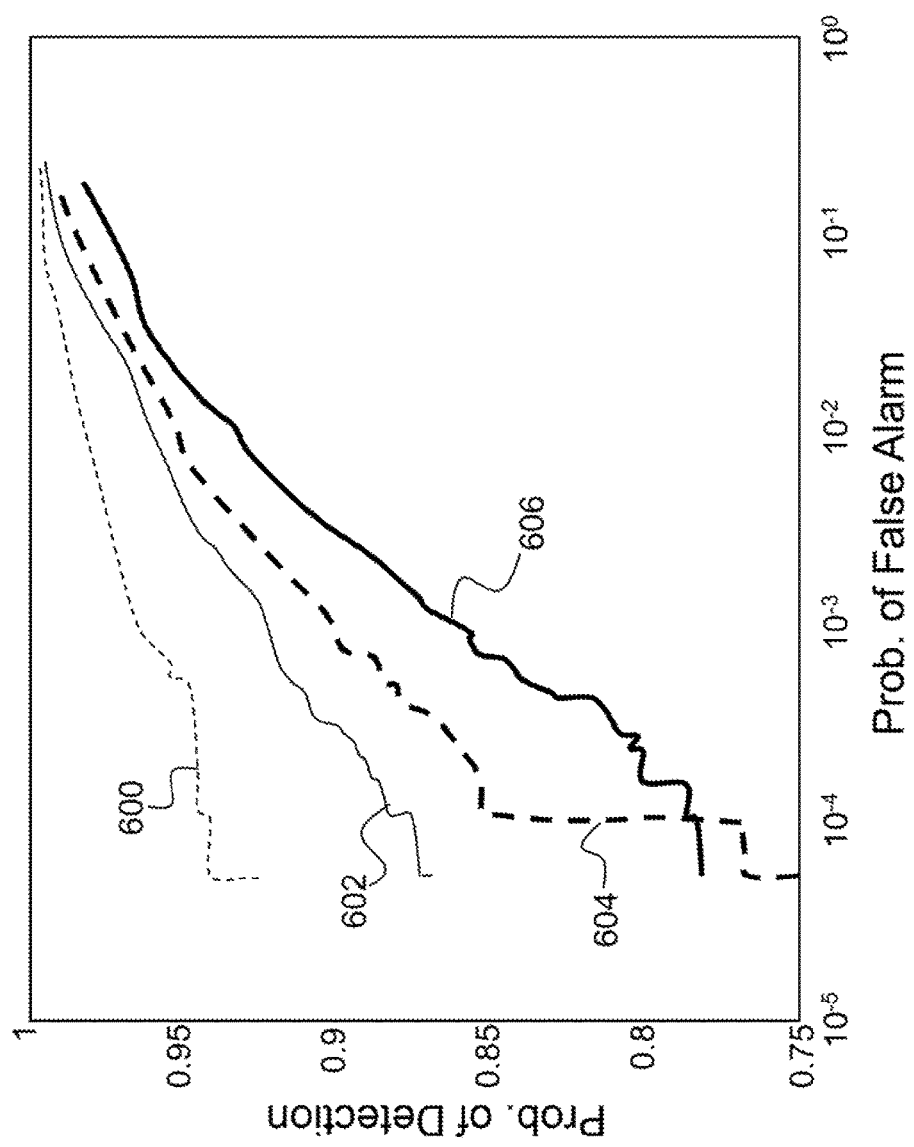
FIG. 6 illustrates a comparison of probability of detection versus probability of false alarms on simulated mixtures of target spectra for varying wavenumber subranges according to various embodiments of the present disclosure.

FIG. 6 is a plot depicting a comparison of SRC $P_d$ versus $P_{fa}$ performance on simulated mixtures of 5 target spectra from a library of 44 explosives for varying wavenumber subranges with fixed PSNR 20 dB from the full URI range ($v \in [650, 4000]$ cm$^{-1}$) to a baseline subrange in longwave infrared (LWIR) ($v \in [870, 1470]$ cm$^{-1}$). Curve 600 represents $v \in [650, 4000]$, curve 602 represents $v \in [870, 1670] \cup [2850, 3125]$, curve 604 represents $v \in [870, 1670]$, and curve 606 represents $v \in [870, 1470]$. Additionally, for the combinations of spectra considered in the experimental studies, increasing the spectral coverage of the spectrometer from the baseline wavenumbers to the inclusion of wavenumbers in the range 1470-1670 cm$^{-1}$ and then further inclusion of the midwave infrared (MWIR) wavenumbers results in progressively better performance.

Figure 7:
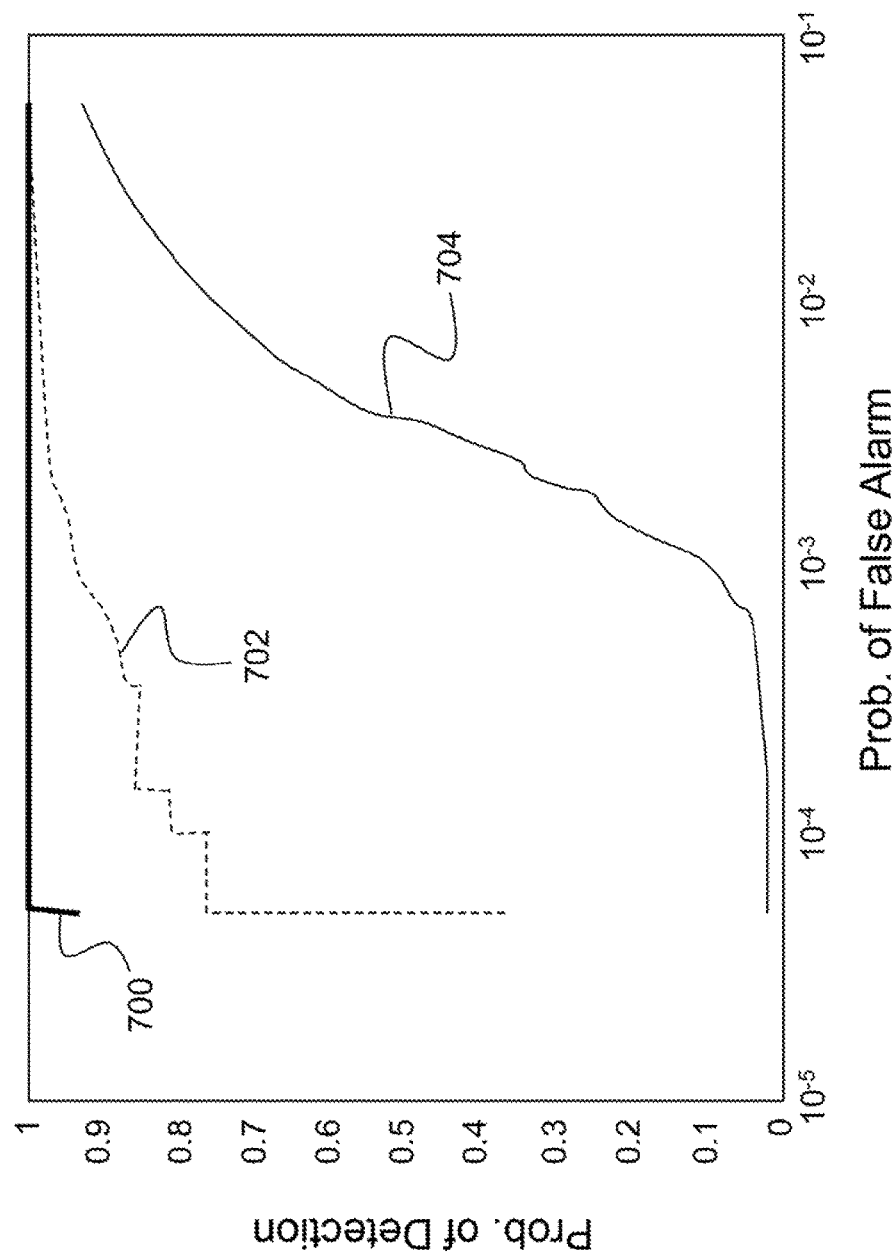
FIG. 7 illustrates the capability of the SRC detection algorithm to identify target compounds mixed together with clutter according to various embodiments of the present disclosure.

In FIG. 7, the effectiveness of SRC for identifying targets in the presence of high magnitude clutter that contains many species and, thus, is spectrally dense is depicted. For each of these simulations, 10 of the URI spectra were designated as belonging to targets of interest, and the remaining 34 were designated as spectra for background clutter. Synthetic mixtures were generated by combining 3 target spectra with 10 background spectra. The mixture weights for the background components were also uniformly random, and the weights for the target components were constrained to be 0.2% (curve 704), 0.5% (curve 702), and 1% (curve 700) of the total weight for the background components, respectively. These results are obtained for PSNR=30 dB. This non-limiting example demonstrates that for sufficiently high PSNR (30 dB), SRC alone is able to achieve good $P_d/P_{fa}$ performance for multiple targets in spectrally dense clutter.

Figure 8:
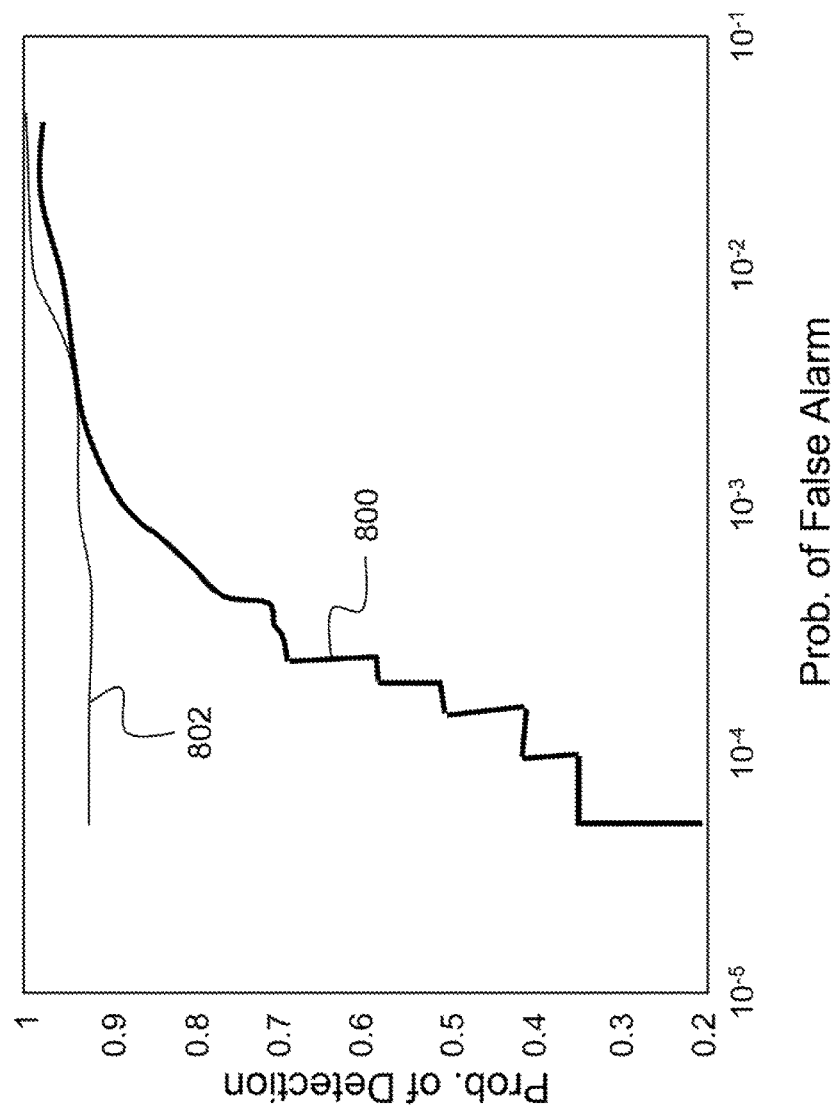
FIG. 8 illustrates the performance increase when the blind unmixing independent component analysis (ICS) algorithm is used to pre-filter the input to the SRC detection algorithm according to various embodiments of the present disclosure.

Finally, in FIG. 8, simulation results are shown that demonstrate the large performance increase possible when using a statistical blind unmixing method, such as ICA (see Literature Reference No. 6), to pre-filter the input to the SRC detection algorithm. In these simulations, random mixtures of 5 explosives that were randomly selected over many runs from the 44 member URI explosives dataset were detected. For each group of 5 spectra, 4 were designated as targets and 1 as clutter. The ROC (receiver operating characteristic) curves shown are the result of simulations done using either the SRC algorithm alone with measurement PSNR of 25 dB (element 800) or the combined ICA/SRC with PSNR of 20 dB (element 802). Combining ICA with SRC (element 802) dramatically improved the performance over SRC alone (element 800). It was also noted that the result for SRC alone (element 800) was done on a spectrum with 538 uniformly spaced wavenumbers in the range between 650 and 4000 cm$^{-1}$. In contrast, for the result obtained when both ICA and SRC (element 802) were used, the spectrum was obtained by foveated sampling with only 88 wave number samples.

Figure 9:
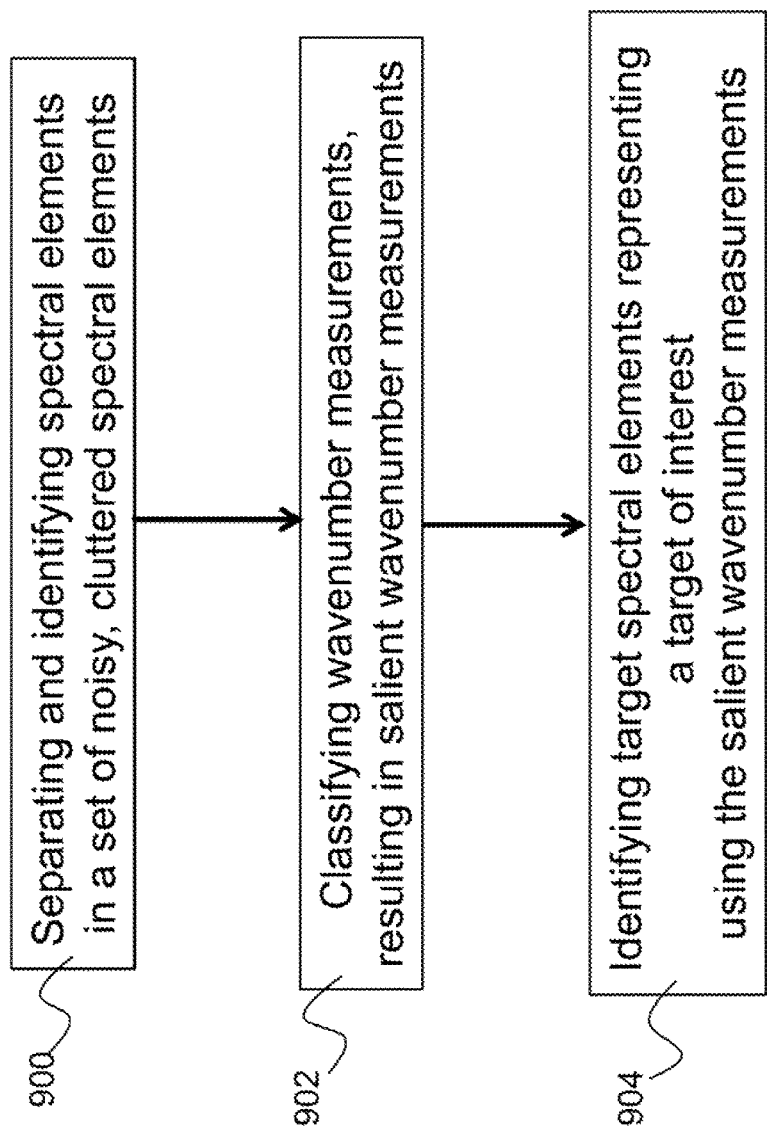
FIG. 9 illustrates a system for library-based spectral demixing according to various embodiments of the present disclosure.

FIG. 9 depicts a system for library-based spectral demising according to various embodiments of the present disclosure. In a first operation 900, the system simultaneously separates and identifies spectral elements in a set of noisy, cluttered spectral elements using SRC. In a second operation 902, wavenumber measurements are classified, resulting in salient wavenumber measurements. In a third operation 904, target spectral elements representing a target of interest are identified using the salient wavenumber measurements.

In summary, the system according to various embodiments of the present disclosure with nonuniform foveated sampling of input spectra used by SRC to model the mixture for reducing the number of measurements required and the computational complexity. SRC is used to simultaneously denoise and identify the spectral components in noisy, cluttered spectra by modeling using a library of spectral templates. Additionally, SRC is used to compensate for corruptions that affect a sparse set of wavenumbers the spectra. Further, SRC is used to model and compensate for spectral deformations with a known smooth parameterized form.

The system described herein is applicable to both lab-based and remote sensing of materials and chemical residues. Additionally, it can be used for hyperspectral imaging data analysis as well as spectral analysis. Further, the system according to various embodiments of the present disclosure is useful for analyzing satellite imagery and improved object recognition, such as in automotive active safety systems or automatic target recognition systems for self-guided weapons and airborne surveillance systems.

Finally, while this invention has been described in terms of several embodiments, one of ordinary skill in the art will readily recognize that the invention may have other applications in other environments. It should be noted that many embodiments and implementations are possible. Further, the following claims are in no way intended to limit the scope of the present invention to the specific embodiments described above. In addition, any recitation of "means for" is intended to evoke a means-plus-function reading of an element and a claim, whereas, any elements that do not specifically use the recitation "means for", are not intended to be read as means-plus-function elements, even if the claim otherwise includes the word "means". Further, while particular method steps have been recited in a particular order, the method steps may occur in any desired order and fall within the scope of the present invention.

What is claimed is:

1. A system for spectral demixing, the system comprising:
one or more processors and a non-transitory computer-readable medium having executable instructions encoded thereon such that when executed, the one or more processors perform operations of:
simultaneously separating and identifying spectral elements in a set of noisy, cluttered spectral elements using Sparse Representation-based Classification (SRC) by modeling the set of noisy, cluttered spectral elements using a spectral library;
wherein the spectral library models each spectral element in the set of noisy, cluttered spectral elements, each spectral element having a corresponding wavenumber measurement;
classifying wavenumber measurements to identify salient wavenumber measurements; and
using foveated nonuniform sampling of salient wavenumber measurements with spectral sensors for target of interest identification.

2. The system as set forth in claim 1, wherein given a context for a class of a target of interest, the one or more processors further perform an operation of discriminating between distinct targets of interest.

3. The system as set forth in claim 1, wherein given a context for a class of a target of interest, the one or more processors further perform an operation of discriminating between targets of interest and clutter.

4. The system as set forth in claim 1, wherein given a context for a class of a target of interest, the one or more processors further perform an operation of determining which wavenumber measurements are relevant to the target of interest using the context for the class of the target of interest.

5. The system as set forth in claim 1, wherein the spectral library includes rows, and wherein the one or more processors further perform an operation of pruning rows of the spectral library that do not correspond to salient wavenumber measurements.

6. A computer-implemented method for spectral demixing, comprising:
an act of causing one or more processors to execute instructions stored on a non-transitory memory such that upon execution, the one or more processors perform operations of:
simultaneously separating and identifying spectral elements in a set of noisy, cluttered spectral elements using Sparse Representation-based Classification (SRC) by modeling the set of noisy, cluttered spectral elements using a spectral library;
wherein the spectral library models each spectral element in the set of noisy, cluttered spectral elements, each spectral element having a corresponding wavenumber measurement;
classifying wavenumber measurements to identify salient wavenumber measurements; and
using foveated nonuniform sampling of salient wavenumber measurements with spectral sensors for target of interest identification.

7. The method as set forth in claim 6, wherein given a context for a class of a target of interest, the one or more processors further perform an operation of discriminating between distinct targets of interest.

8. The method as set forth in claim 6, wherein given a context for a class of a target of interest, the one or more processors further perform an operation of discriminating between targets of interest and clutter.

9. The method as set forth in claim 6, wherein given a context for a class of a target of interest, the one or more processors further perform an operation of determining which wavenumber measurements are relevant to the target of interest using the context for the class of the target of interest.

10. The method as set forth in claim 6, wherein the spectral library includes rows, and wherein the one or more processors further perform an operation of pruning rows of the spectral library that do not correspond to salient wavenumber measurements.

11. A computer program product for spectral demixing, the computer program product comprising:
   computer-readable instructions stored on a non-transitory computer-readable medium that are executable by a computer having one or more processors for causing the processor to perform operations of:
   simultaneously separating and identifying spectral elements in a set of noisy, cluttered spectral elements using Sparse Representation-based Classification (SRC) by modeling the set of noisy, cluttered spectral elements using a spectral library;
   wherein the spectral library models each spectral element in the set of noisy, cluttered spectral elements, each spectral element having a corresponding wavenumber measurement;
   classifying wavenumber measurements to identify salient wavenumber measurements; and
   using foveated nonuniform sampling of salient wavenumber measurements with spectral sensors for target of interest identification.

12. The computer program product as set forth in claim 11, wherein given a context for a class of a target of interest, the computer program product further comprises instructions for causing the one or more processors to further perform an operation of discriminating between distinct targets of interest.

13. The computer program product as set forth in claim 11, wherein given a context for a class of a target of interest, the computer program product further comprises instructions for causing the one or more processors to further perform an operation of discriminating between targets of interest and clutter.

14. The computer program product as set forth in claim 11, wherein given a context for a class of a target of interest, the computer program product further comprises instructions for causing the one or more processors to further perform an operation of determining which wavenumber measurements are relevant to the target of interest using the context for the class of the target of interest.

15. The computer program product as set forth in claim 11, wherein the spectral library includes rows, and wherein the computer program product further comprises instructions for causing the one or more processors to further perform an operation of pruning rows of the spectral library that do not correspond to salient wavenumber measurements.

* * * * *